United States Patent
Tsukazaki et al.

(10) Patent No.: US 12,377,399 B2
(45) Date of Patent: Aug. 5, 2025

(54) ACTIVATED CARBON FOR ADSORBING MOLECULAR POLAR SUBSTANCE

(71) Applicants: KANSAI COKE AND CHEMICALS CO., LTD., Hyogo (JP); MC Evolve Technologies Corporation, Hyogo (JP)

(72) Inventors: Takaki Tsukazaki, Amagasaki (JP); Kojiro Tenno, Amagasaki (JP); Yoji Ichiraku, Amagasaki (JP); Hiroyuki Ito, Kakogawa (JP)

(73) Assignees: KANSAI COKE AND CHEMICALS CO., LTD., Hyogo (JP); MC EVOLVE TECHNOLOGIES CORPORATION, Hyogo (JP)

( * ) Notice: Subject to any disclaimer, the term of this patent is extended or adjusted under 35 U.S.C. 154(b) by 661 days.

(21) Appl. No.: 17/779,314

(22) PCT Filed: Sep. 30, 2020

(86) PCT No.: PCT/JP2020/037324
§ 371 (c)(1),
(2) Date: May 24, 2022

(87) PCT Pub. No.: WO2021/106364
PCT Pub. Date: Jun. 3, 2021

(65) Prior Publication Data
US 2022/0410119 A1    Dec. 29, 2022

(30) Foreign Application Priority Data
Nov. 25, 2019    (JP) .................................. 2019-212411

(51) Int. Cl.
B01J 20/20    (2006.01)
A61L 9/014    (2006.01)
(Continued)

(52) U.S. Cl.
CPC ............... B01J 20/20 (2013.01); A61L 9/014 (2013.01); B01J 20/28061 (2013.01);
(Continued)

(58) Field of Classification Search
None
See application file for complete search history.

(56) References Cited

U.S. PATENT DOCUMENTS
2015/0203356 A1    7/2015    Yasumaru et al.

FOREIGN PATENT DOCUMENTS
JP    2002-159852    6/2002
JP    2004-315243    11/2004
(Continued)

OTHER PUBLICATIONS

International Search Report issued Nov. 17, 2020 in International (PCT) Application No. PCT/JP2020/037324.
(Continued)

*Primary Examiner* — Daniel Berns
(74) *Attorney, Agent, or Firm* — Wenderoth, Lind & Ponack, L.L.P.

(57) ABSTRACT

The present invention aims to provide an activated carbon for adsorbing a molecular polar substance with excellent adsorption property to a molecular polar substance and regeneratability. The present invention provides an activated carbon for adsorbing a molecular polar substance obtained by an alkali activation method, wherein the activated carbon has an acidic functional group in an amount of 2.1 meq/g or more, a basic functional group in an amount of more than 0 to 0.6 meq/g, and a specific surface area of 1000 to 4000 $m^2/g$.

7 Claims, 8 Drawing Sheets

(51) Int. Cl.
  *B01J 20/28* (2006.01)
  *C01B 32/348* (2017.01)
  *C02F 1/28* (2023.01)
  *C02F 101/38* (2006.01)

(52) U.S. Cl.
  CPC ... *B01J 20/28064* (2013.01); *B01J 20/28066* (2013.01); *C01B 32/348* (2017.08); *C02F 1/283* (2013.01); *A61L 2209/22* (2013.01); *C01P 2006/12* (2013.01); *C02F 2101/38* (2013.01); *C02F 2307/06* (2013.01)

(56) References Cited

FOREIGN PATENT DOCUMENTS

| | | | | |
|---|---|---|---|---|
| JP | 2017-172099 | | 9/2017 | |
| JP | 2017172099 A | * | 9/2017 | ............... D01F 9/22 |
| JP | 2019-98324 | | 6/2019 | |
| WO | 2014/017588 | | 1/2014 | |

OTHER PUBLICATIONS

Office Action issued Oct. 7, 2023 in corresponding Chinese Patent Application No. 202080080875.0 with English-language translation.

Office Action issued Jul. 5, 2024 in Chinese Patent Application No. 202080080875.0, with English-language Translation.

Japanese Office Action issued Sep. 5, 2023 in corresponding Japanese Patent Application No. 2021-561194, with English machine translation.

Office Action issued Apr. 3, 2024 in corresponding Chinese Patent Application No. 202080080875.0, with English language translation.

Request for the Submission of an Opinion issued Apr. 10, 2025 in corresponding Korean Patent Application No. 10-2022-7019447, with English language translation.

* cited by examiner

[FIG. 1]
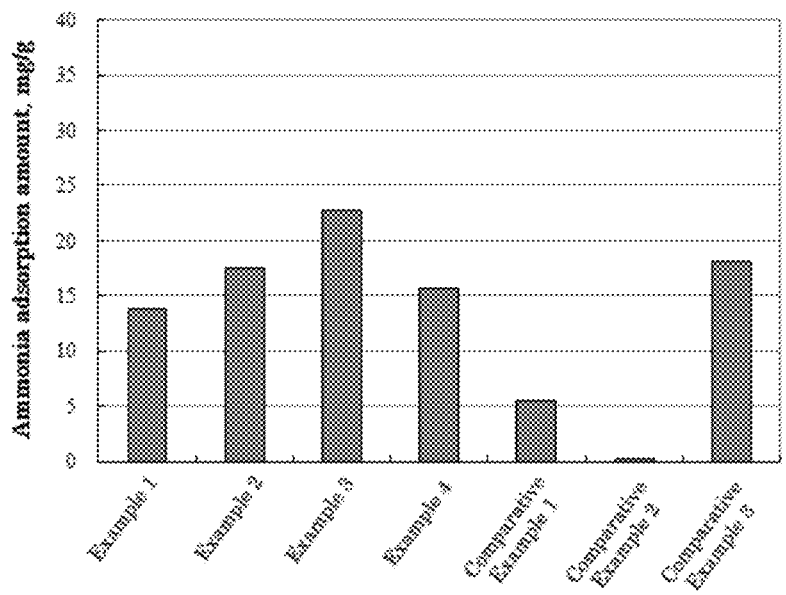
[FIG. 2]
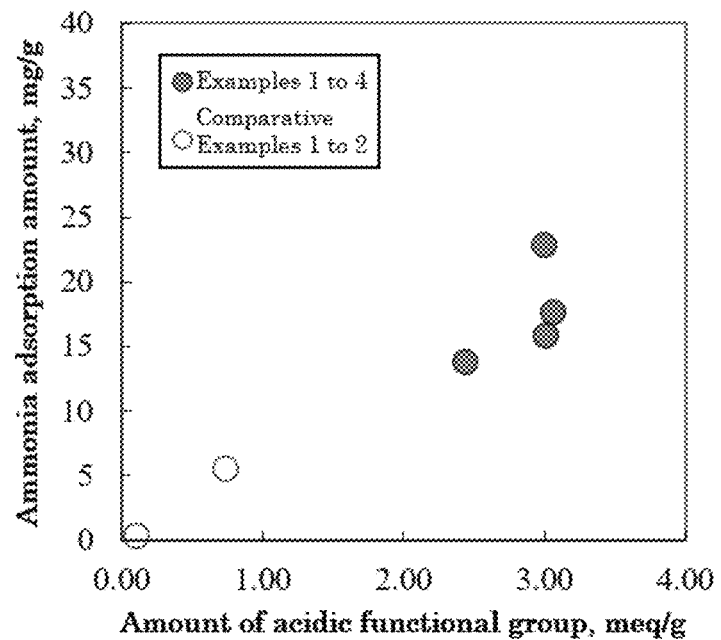

[FIG. 3]
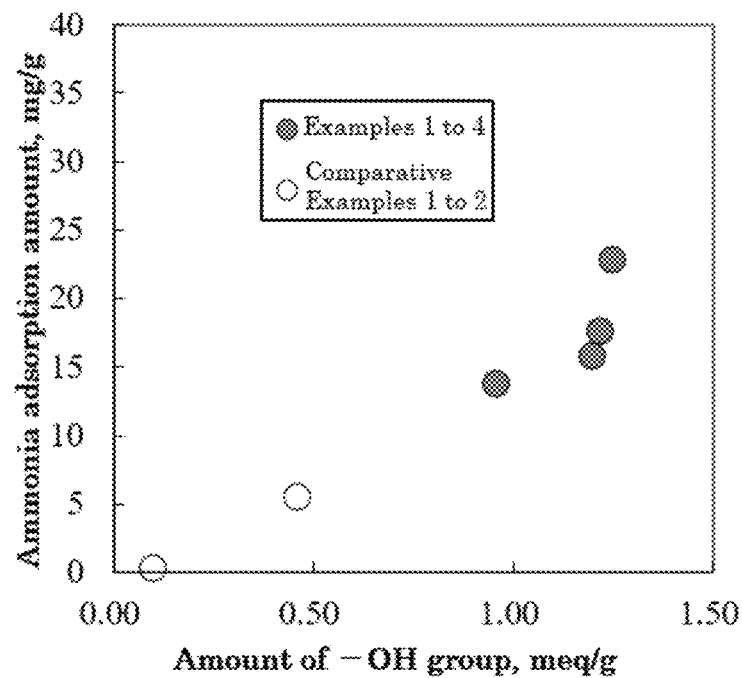
[FIG. 4]
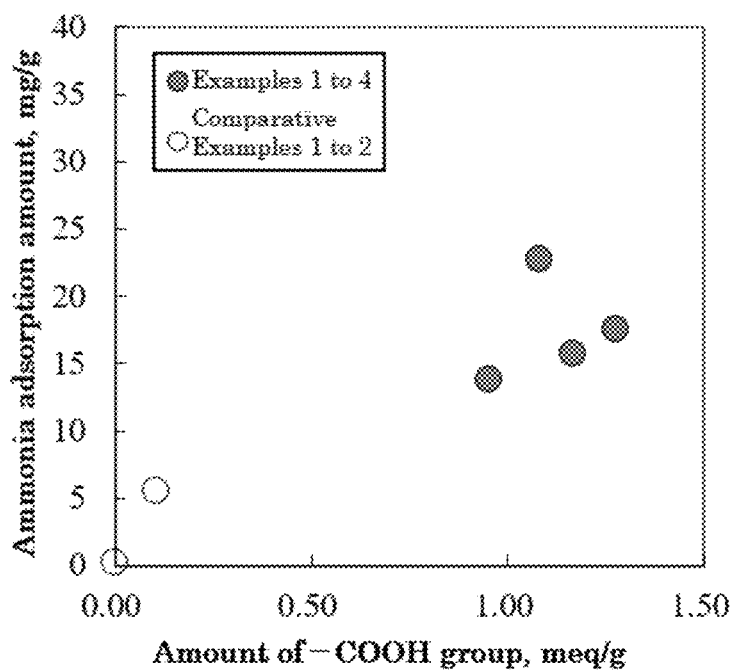

[FIG. 5]
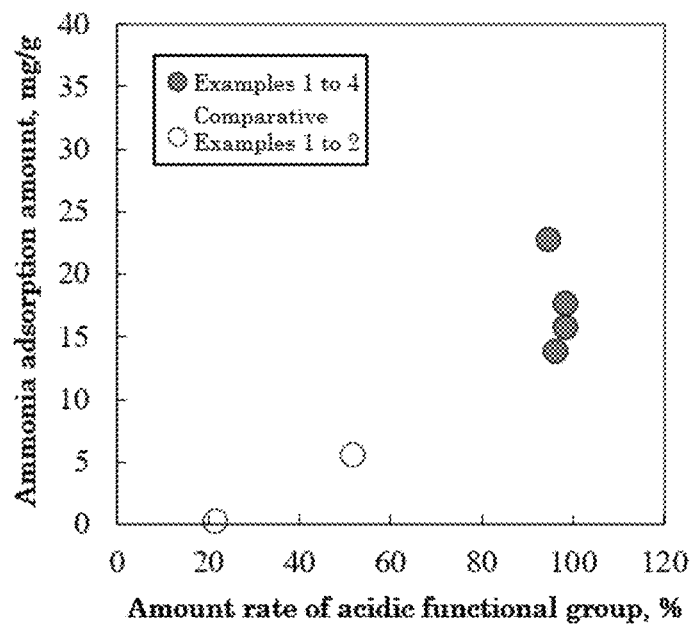
[FIG. 6]
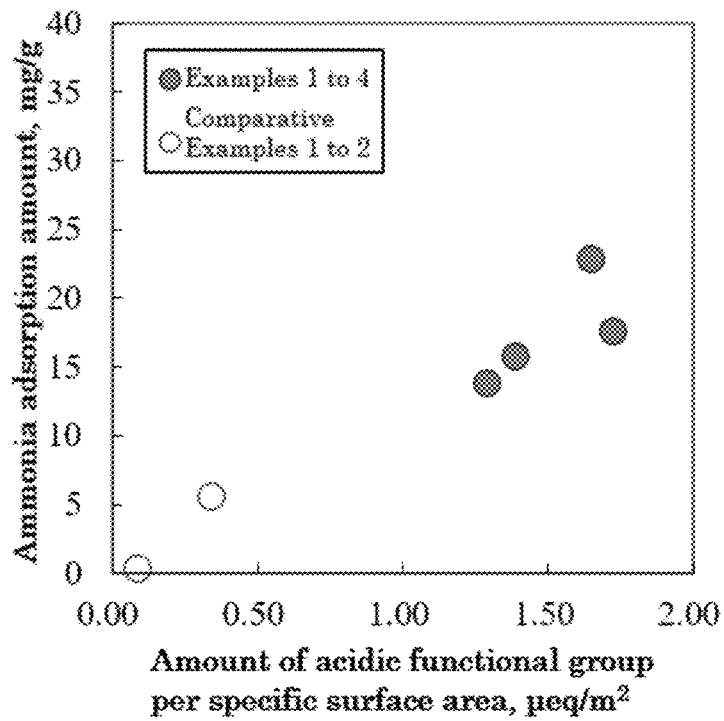

[FIG. 7]
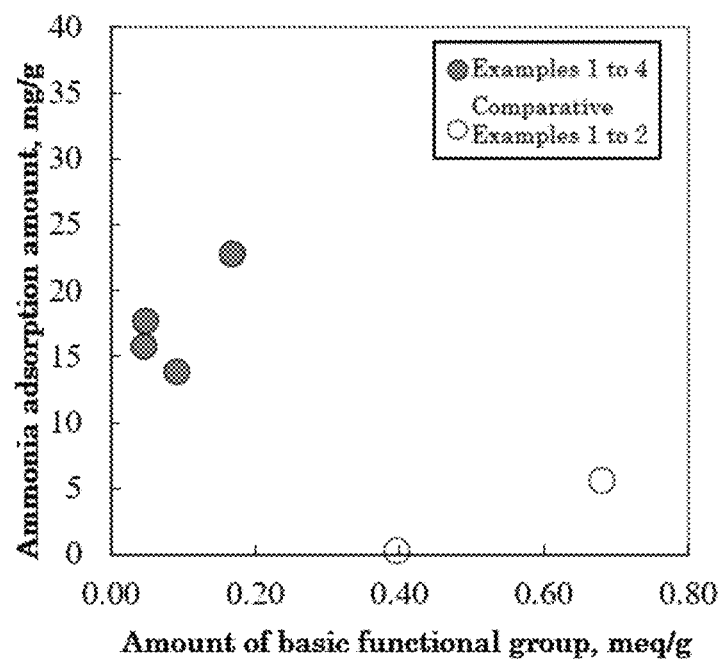
[FIG. 8]
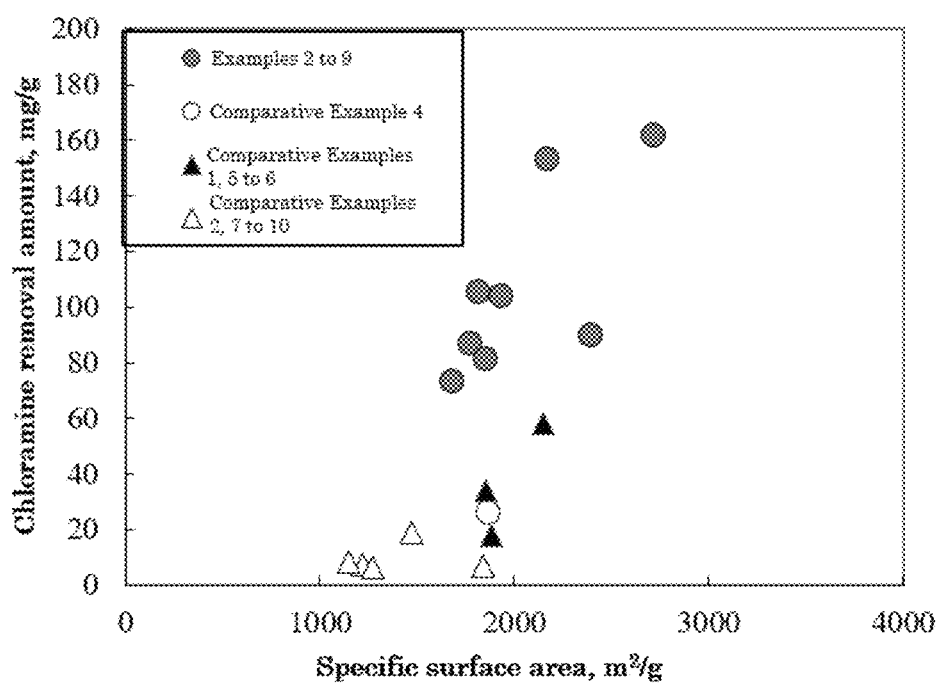

[FIG. 9]
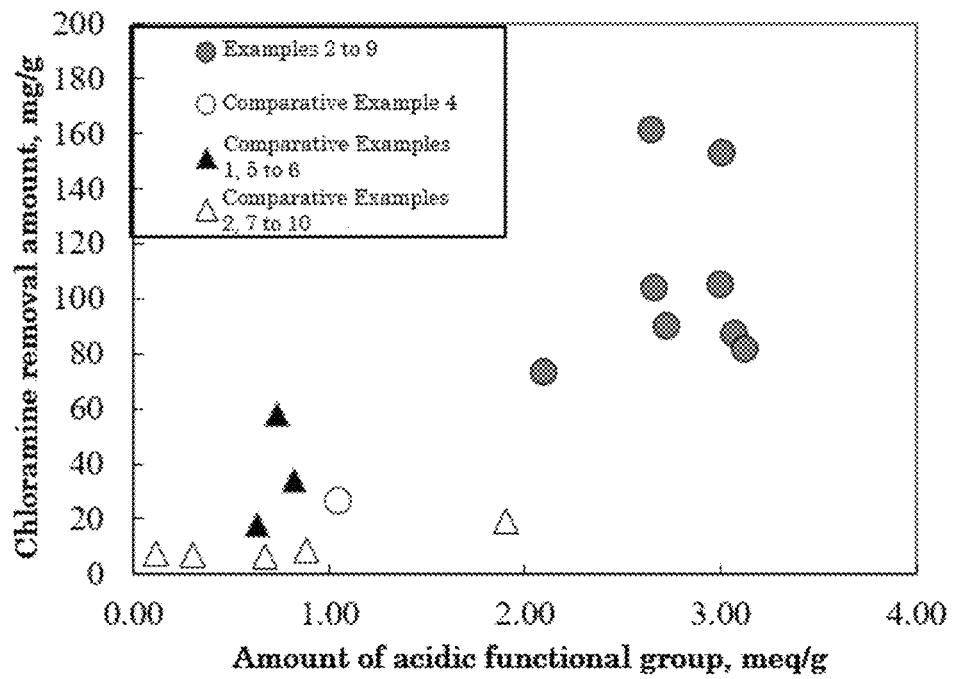
[FIG. 10]
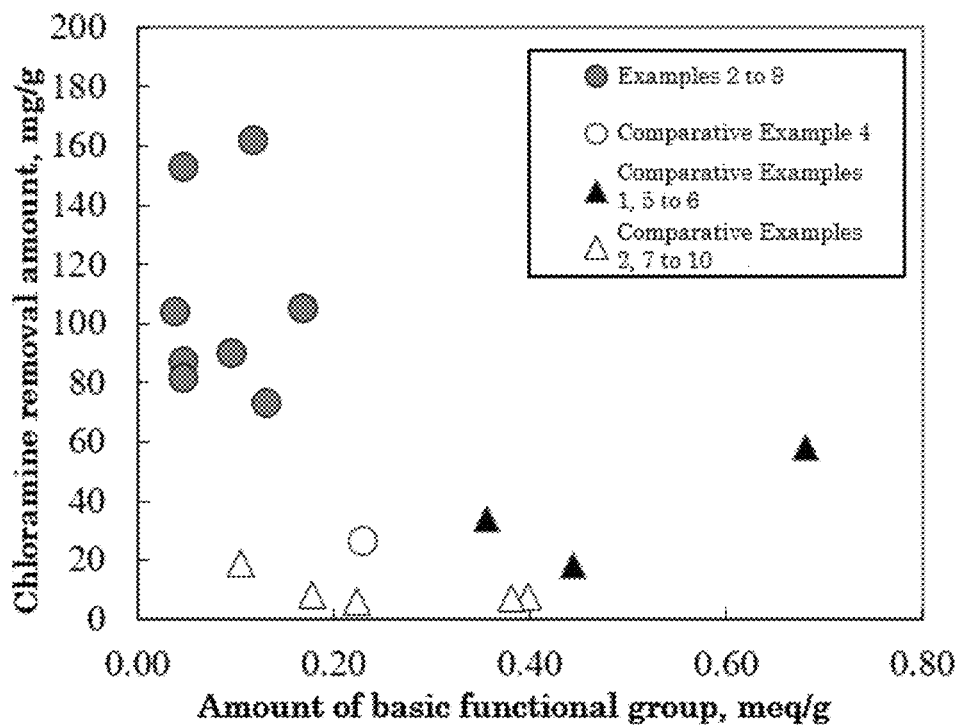

[FIG. 11]
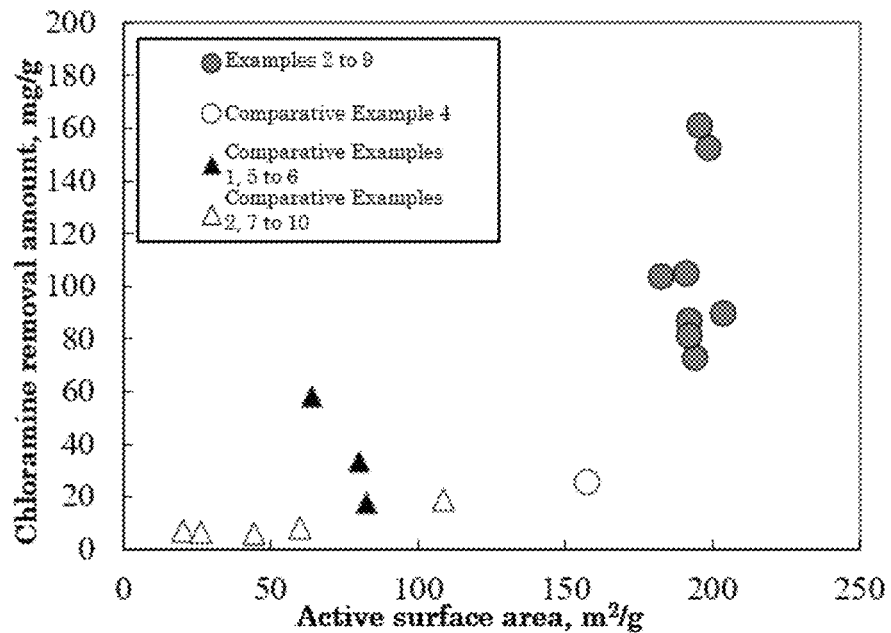
[FIG. 12]
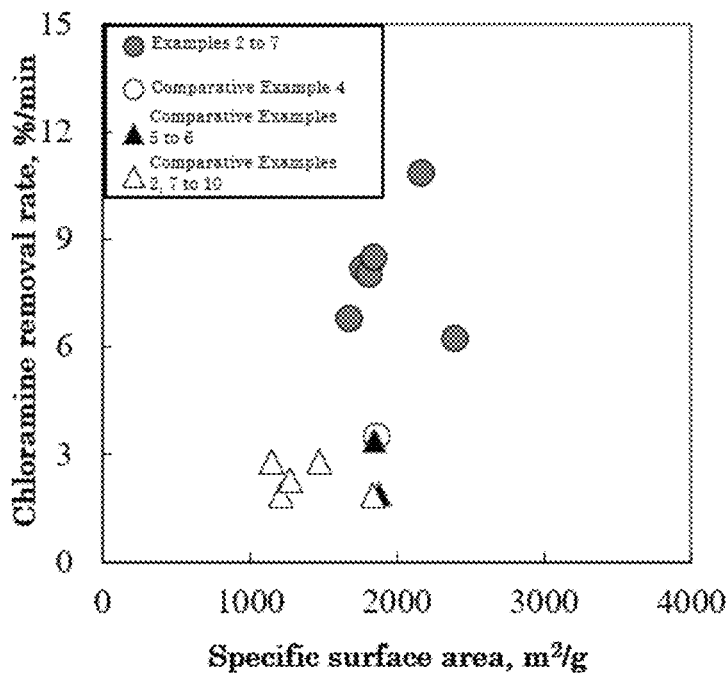

[FIG. 13]
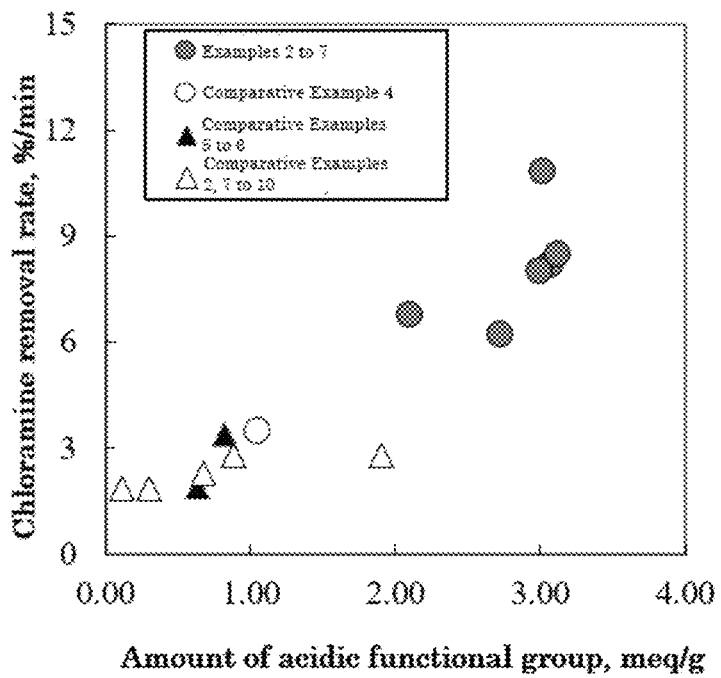
[FIG. 14]
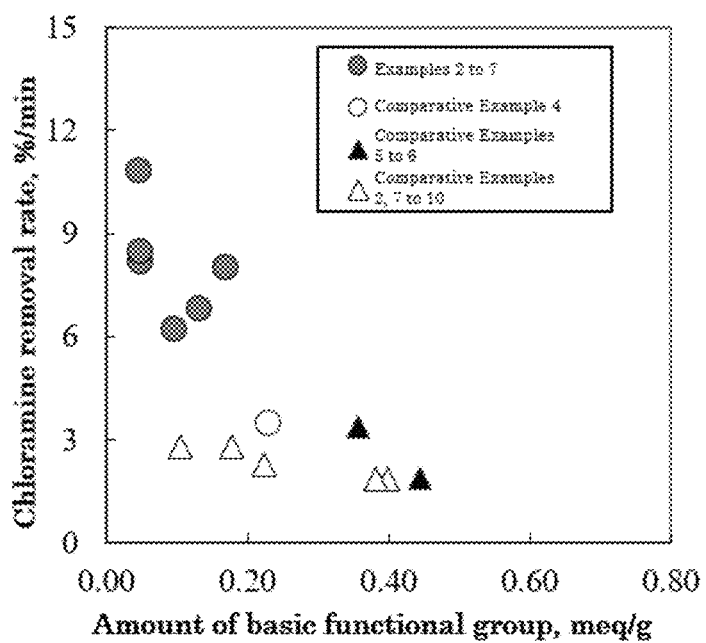

[FIG. 15]
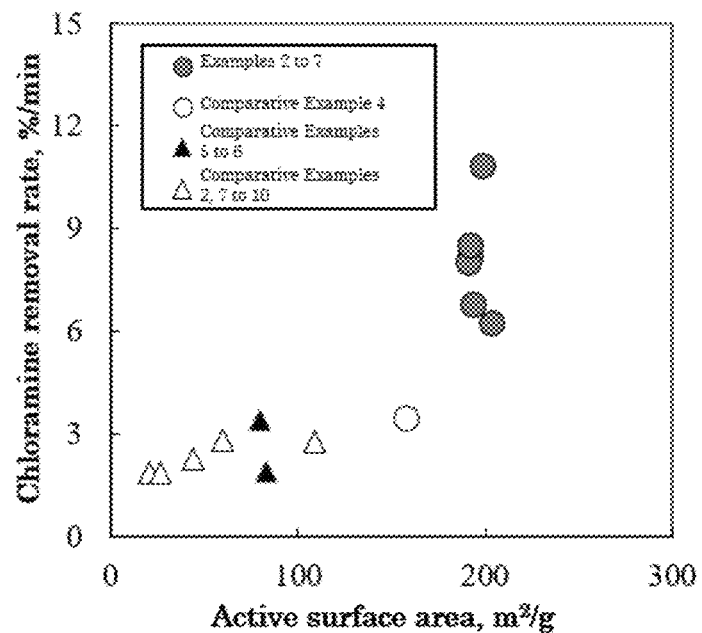
[FIG. 16]
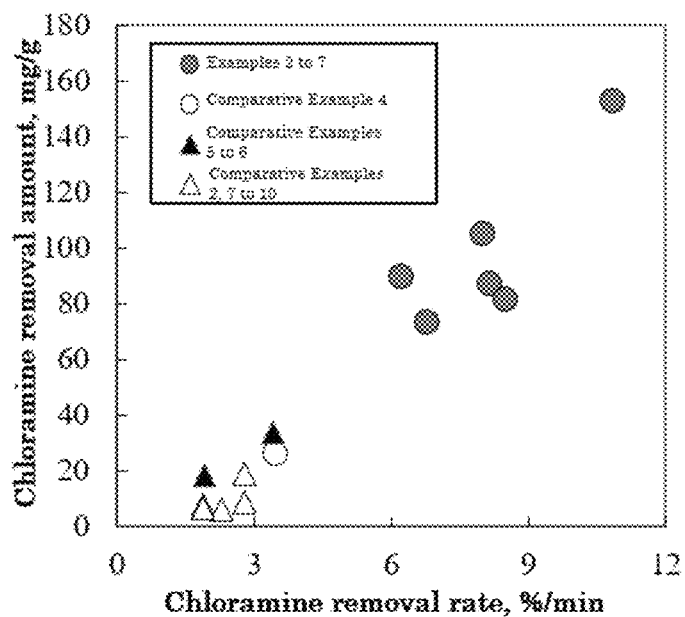

ACTIVATED CARBON FOR ADSORBING MOLECULAR POLAR SUBSTANCE

TECHNICAL FIELD

The present invention relates to activated carbon for adsorbing a molecular polar substance. In particular, the present invention relates to activated carbon having excellent adsorption property of a molecular polar substance.

BACKGROUND ART

Activated carbon having high specific surface area is widely used as an adsorption material. For example, activated carbon is used to remove odor causing substance such as ammonia, chloramine, or the like. In recent years, modification techniques of activated carbon have been suggested to improve adsorption property for specific substances.

For examples, Patent Document 1 discloses the activated carbon having phosphoric acid impregnated in pores to improve adsorption property to ammonia in gas phase. This activated carbon exhibits excellent adsorption property to ammonia by chemically adsorbing ammonia to phosphoric acid in pores.

Also, Patent Document 2 discloses the activated carbon having specific surface area of about 500 to 900 $m^2/g$, increased amount of total acidic functional groups (around 1.0 to 2.4 meq/g), and increased amount of acidic functional groups originated from carboxylic acids (around 0.2 to 0.9 meq/g) to improve adsorption property to trace metal in liquid phase. This activated carbon exhibits excellent adsorption property to trace metal in liquid phase by increasing the amount of acidic functional groups.

Furthermore, Patent Document 3 discloses the activated carbon having adjusted amount of surface oxide (0.35 meq/g or more) on surface of the activated carbon and BET specific surface area (900 to 2020 $m^2/g$) to improve adsorption property to polar substances. This activated carbon has chemically adsorbing ability to polar substances and adsorption ability derived from pores of activated carbon.

PRIOR ART DOCUMENT

Patent Documents

Patent Document 1: Japanese Laid-open Patent Publication No. 2002-159852
Patent Document 2: Japanese Laid-open Patent Publication No. 2004-315243
Patent Document 3: Japanese Laid-open Patent Publication No. 2019-098324

SUMMARY OF THE INVENTION

Problems to be Solved by the Invention

Unmodified Activated carbon can be used either in liquid or gas phase, and the activated carbon is modified corresponding to its usage environment when modifying its adsorption property. For Example, the activated carbon with impregnated chemical agent such as phosphoric acid as described in Patent Document 1 is suitable for removing ammonia in gas phase, however the activated carbon cannot be used in liquid phase for the impregnated chemical agent is out flown from the activated carbon. Usually, activated carbon with impregnated chemical agent cannot be reused after adsorbing adsorbate because cleaning the activated carbon washes away impregnated chemical agent as well as adsorbate. The activated carbon with increased amount of acidic functional groups and suppressed specific surface area as described in Patent Document 2 is suitable for adsorbing metals in liquid phase, however, the activated carbon has insufficient adsorption property due to its low adsorption capacity. The activated carbon of Patent Document 3 does not have sufficient adsorption rate, for example, to chloramine.

The present invention has accomplished to solve the above problem, it is an object of the present invention to provide an activated carbon for adsorbing a molecular polar substance with excellent adsorption property to a molecular polar substance and regeneratability.

Means to Solve the Problems

The present invention which solved above-described problem is as follows.

[1] An activated carbon for adsorbing a molecular polar substance obtained by an alkali activation method, wherein the activated carbon has an acidic functional group in an amount of 2.1 meq/g or more, a basic functional group in an amount of more than 0 to 0.6 meq/g, and a specific surface area of 1000 to 4000 $m^2/g$.

[2] The activated carbon for adsorbing a molecular polar substance according to [1], wherein the acidic functional group contains a hydroxy group and a carboxy group in a total amount of 0.6 meq/g or more.

[3] The activated carbon for adsorbing a molecular polar substance according to [1] or [2], wherein a ratio of the acidic functional group amount to the total of the acidic functional group amount and the basic functional group amount is 70% or more.

[4] The activated carbon for adsorbing a molecular polar substance according to any one of [1] to [3], wherein the activated carbon has the acidic functional group of 0.7 μeq/$m^2$ or more per specific surface area.

[5] The activated carbon for adsorbing a molecular polar substance according to any one of [1] to [4], wherein the activated carbon has no chemical agent impregnated pores.

[6] The activated carbon for adsorbing a molecular polar substance according to any one of [1] to [5], wherein the activated carbon has an active surface area of 180 $m^2/g$ or more.

Effects of the Invention

The activated carbon for adsorbing a molecular polar substance of the present invention has high specific surface area and increased amount of acidic functional groups, therefore, the activated carbon has excellent adsorption property to a molecular polar substance. The activated carbon for adsorbing a molecular polar substance of the present invention adsorbs molecular polar substances to the acidic functional groups, allowing the activated carbon to be regenerated as an adsorber for the acidic surface functional groups remaining in the activated carbon after conducting regeneration process such as washing.

BRIEF DESCRIPTION OF THE DRAWINGS

FIG. 1 is a graph showing ammonia adsorption amount of activated carbons of Examples.

FIG. 2 is a graph showing the relationship of ammonia adsorption amount to amount of acidic functional group of the activated carbons of Examples.

FIG. 3 is a graph showing relationship of ammonia adsorption amount to amount of OH group of the activated carbons of Examples.

FIG. 4 is a graph showing the relationship of ammonia adsorption amount to amount of COOH group of the activated carbons of Examples.

FIG. 5 is a graph showing the relationship of ammonia adsorption amount to amount rate of acidic functional group of the activated carbons of Examples.

FIG. 6 is a graph showing the relationship of ammonia adsorption amount to amount of acidic functional group per specific surface area of the activated carbons of Examples.

FIG. 7 is a graph showing the relationship of ammonia adsorption amount to amount of basic functional group of the activated carbons of Examples.

FIG. 8 is a graph showing the relationship of chloramine removal amount to specific surface area of the activated carbons of Examples.

FIG. 9 is a graph showing the relationship of chloramine removal amount to amount of acidic functional group of the activated carbons of Examples.

FIG. 10 is a graph showing the relationship of chloramine removal amount to amount of basic functional group of the activated carbons of Examples.

FIG. 11 is a graph showing the relationship of chloramine removal amount to active surface area of the activated carbons of Examples.

FIG. 12 is a graph showing the relationship of chloramine removal rate to specific surface area of the activated carbons of Examples.

FIG. 13 is a graph showing the relationship of chloramine removal rate to amount of acidic functional group of the activated carbons of Examples.

FIG. 14 is a graph showing the relationship of chloramine removal rate to amount of basic functional group of the activated carbons of Examples.

FIG. 15 is a graph showing the relationship of chloramine removal rate to active surface area of the activated carbons of Examples.

FIG. 16 is a graph showing the relationship of chloramine removal amount to chloramine removal rate of the activated carbons of Examples.

MODE FOR CARRYING OUT THE INVENTION

The present inventors have investigated activated carbon aiming to improve the adsorption property to a molecular polar substance as well as to offer regeneratable activated carbon. At first, the activated carbon having enlarged specific surface area was contacted with ammonia-containing gas, however, the activated carbon showed poor adsorption property to ammonia. Also, the activated carbon with increased amount of acidic functional groups as shown in Patent Document 2 showed poor adsorption property due to its small specific surface area. The inventors thought that the adsorption property to a molecular polar substance could be improved by enlarging the specific surface area to increase adsorption capacity as well as enlarging an edge surface of the activated carbon to increase the amount of acidic functional groups. However, the enlargement of specific surface area results in decreasing the amount of acidic functional groups and therefore, it has been difficult to achieve both enlarging specific surface area and increasing the amount of acidic functional groups at the same time. The present inventors re-examined manufacturing conditions of activated carbon and reached the present invention by finding that different manufacturing conditions from conventional manufacturing conditions, that is, optimization of activation conditions such as conducting alkali activation at low temperature allows both of specific surface area and amount of acidic functional groups to increase, providing an activated carbon suitable for adsorbing a molecular polar substance.

In the present invention, adsorption property of activated carbon is adsorption amount and/or adsorption rate of the activated carbon against a molecular polar substance existing in gas and/or liquid phase.

Properties of the activated carbon of the present invention is measured by the methods described in Examples, unless otherwise specified.

The present inventive activated carbon for adsorbing a molecular polar substance is obtained by alkali-activation method and has acidic functional groups in an amount of 2.1 meq/g or more, basic functional groups in an amount of more than 0 to 0.6 meq/g, and specific surface area of 1000 to 4000 $m^2/g$.

Activated Carbon for Adsorbing a Molecular Polar Substance

In the present invention, the activated carbon for adsorbing a molecular polar substance is the activated carbon having adsorption property to a molecular polar substance. A molecular polar substance is the substance whose molecules have electric polarity, and the examples of the molecular polar substances include the compounds having polar groups such as amino group, halogen group, hydroxy group, carboxy group, nitro group, formyl group, alkoxy group, ester group, and nitrile group. Specific examples of the compounds are malodorous components such as trimethylamine, hydrogen sulfide, ammonia, and methyl mercaptan; volatile organic compounds (VOC) such as formaldehyde, toluene, xylene, ethylbenzene, styrene, and acetaldehyde; sterilizers for tap water such as chloramine and hypochlorite.

Specific Surface Area

The present inventive activated carbon for adsorbing a molecular polar substance has the specific surface area of 1000 to 4000 $m^2/g$. As the specific surface area increases, adsorption amount of a molecular polar substance increases and also edge surface in pores increases to improve adsorption property. On the other hand, as the specific surface area excessively increases, the amount of acidic functional groups decreases and adsorption force to a molecular polar substance in pores decreases. The specific surface area of the activated carbon for adsorbing a molecular polar substance is preferably 1250 $m^2/g$ or more, more preferably 1500 $m^2/g$ or more, further preferably 1700 $m^2/g$ or more, the most preferably 1800 $m^2/g$ or more, and preferably 3800 $m^2/g$ or less, more preferably 3500 $m^2/g$ or less, further preferably 3000 $m^2/g$ or less, and the most preferably 2500 $m^2/g$ or less.

Amount of Acidic Functional Groups

The present inventive activated carbon for adsorbing a molecular polar substance has acidic functional groups in an amount of 2.1 meq/g or more. Adsorption property to a molecular polar substance can be improved by increasing the amount of acidic functional groups under the specific surface area within above described range. The amount of acidic functional groups is preferably 2.3 meq/g or more, more preferably 2.5 meq/g or more, further preferably 2.7 meq/g or more. Upper limit of the amount of acidic functional groups is not particularly limited, and the amount is preferably 10.0 meq/g or less, more preferably 7.0 meq/g or less, and further preferably 5.0 meq/g or less.

Amount of Basic Functional Groups

The present inventive activated carbon for adsorbing a molecular polar substance has basic functional groups in an amount of more than 0 to 0.6 meq/g. As the amount of basic functional groups excessively increases, the amount of acidic functional groups decreases to lower the adsorption property of a molecular polar substance. On the other hand, basic functional groups cannot be completely removed, so the lower limit of basic functional groups is more than 0. The amount of basic functional groups is preferably 0.5 meq/g or less, more preferably 0.4 meq/g or less, further preferably 0.3 meq/g or less, and preferably 0.001 meq/g or more, more preferably 0.003 meq/g or more.

Ratio of Acidic Functional Group Amount

In teams of enhancing the adsorption property to a molecular polar substance, the ratio of acidic functional groups amount to the sum of acidic functional groups and basic functional groups (amount of acidic functional group/(amount of acidic functional group+amount of basic functional group)×100) is preferably 70% or more, more preferably 80% or more, further preferably 90% or more, and the most preferably 95% or more.

Alkali Activation Method

The present inventive activated carbon for adsorbing a molecular polar substance is the alkali activated carbon obtained by an alkali activation method. Alkali activation of a material to be activated yields pore structure different from pore structure famed by other activation method such as vapor activation, allowing the alkali activated carbon to attain both high specific surface area and large amount of acidic functional groups. The alkali activated carbon of the present invention has pore structure contributing to enhance the carbon's adsorption property compared with the pore structure of vapor activated carbon. The alkali activation method is exemplified in alkali activation treatment process described later. Residues of alkali metal such as potassium may exist in the activated carbon generated in alkali activation treatment as described later.

Sum Amount of Hydroxy Group and Carboxy Group

The present inventive the activated carbon for adsorbing a molecular polar substance contains hydroxy group and carboxy group as a functional group constituting above described acidic functional groups. Preferably, increased content amount of hydroxy group and carboxy group can further improve adsorption property of a molecular polar substance of activated carbon. The sum amount of hydroxy group and carboxy group is preferably 0.6 meq/g or more, more preferably 0.8 meq/g or more, further preferably 1.0 meq/g or more, and the most preferably 1.5 meq/g or more. The upper limit of the sum amount is not particularly restricted, and the sum amount is preferably 10.0 meq/g or less, more preferably 7.0 meq/g or less, and further preferably 5.0 meq/g or less.

The adsorption property to a molecular polar substance takes into account, the activated carbon of the present invention contains hydroxy group and carboxy group respectively in an amount of preferably 0.3 meq/g or more, more preferably 0.5 meq/g or more, further preferably 0.9 meq/g or more, and the most preferably 1.0 meq/g or more.

Amount of Acidic Functional Group Per Specific Surface Area

The increase in both of specific surface area and the amount of acidic functional groups is effective to improve adsorption property to a molecular polar substance. The amount of acidic functional groups per specific surface area of the activated carbon for adsorbing a molecular polar substance is preferably 0.7 $\mu eq/m^2$ or more, more preferably 1.0 $\mu eq/m^2$ or more, and further preferably 1.2 $\mu eq/m^2$ or more.

Active Surface Area

Active surface area (edge surface) with a certain level or more extremely improves adsorption property to a polar substance. The active surface area is preferably 180 $m^2/g$ or more, more preferably 185 $m^2/g$ or more, and further preferably 190 $m^2/g$ or more.

The upper limit is not particularly limited, for the adsorption property of the activated carbon increases as the active surface area increases. The activated carbon shows excellent adsorption property even when the upper is limited to preferably 500 $m^2/g$ or less, more preferably 350 $m^2/g$ or less, and further preferably 250 $m^2/g$ or less.

Pore Volume

When the pore volume of the activated carbon adsorbing a molecular polar substance is too low, the activated carbon of the present invention may not have sufficient adsorption amount of a molecular polar substance. Too large volume of the fine pore may allow the activated carbon to be bulky enough to decrease filling level of activated carbon at the time of use. In the present invention, fine pore volume of the activated carbon for adsorbing a molecular polar substance is preferably 0.3 $cm^3/g$ or more, more preferably 0.6 $cm^3/g$ or more, further preferably 0.8 $cm^3/g$ or more, and preferably 3.0 $cm^3/g$ or less, more preferably 2.5 $cm^3/g$ or less, and further preferably 2.0 $cm^3/g$ or less.

Average Pore Diameter

Too small average pore diameter of the activated carbon for adsorbing a molecular polar substance may decrease diffusiveness of a molecular polar substance, resulting in poor adsorption property to a molecular polar substance. On the other hand, too large average pore diameter may allow the activated carbon to be bulky enough to decrease the filling level of activated carbon at the time of use. The present inventive activated carbon for adsorbing a molecular polar substance has the average pore diameter of preferably 0.5 nm or more, more preferably 1.0 nm or more, further preferably 1.5 nm or more, the most preferably 1.8 nm or more and preferably 5.0 nm or less, more preferably 4.5 nm or less, and further preferably 4.0 nm or less.

The present inventive activated carbon for adsorbing a molecular polar substance has high specific surface area as well as high amount of acidic functional groups suitable for the adsorption of a molecular polar substance, therefore, the activated carbon has excellent adsorption property. Accordingly, the present inventive activated carbon for adsorbing a molecular polar substance needs not to use chemical agent such as phosphoric acid contributing adsorption in a pore.

Also, the present inventive activated carbon for adsorbing a molecular polar substance has the acidic functional groups famed on an edge surface of the activated carbon. Therefore, the acidic functional groups remain on the surface of the activated carbon even when the adsorbed molecular polar substance is removed by the treatment such as washing which allows the activated carbon to be reused as an adsorption material. The present inventive activated carbon for adsorbing a molecular polar substance shows the adsorption rate of, for example, 90% or more after regeneration treatment compared to the activated carbon before the regeneration treatment.

The present inventive activated carbon for adsorbing a molecular polar substance is not restricted in its shape, the activated carbon may take any shape corresponding to the purpose of use, and the examples of the shape include powder form, granular from, fiber form, or grain from.

The present inventive activated carbon for adsorbing a molecular polar substance measures its values of physical properties such as specific surface area and fine pore volume as well as surface functional groups amount such as acidic functional group amount and basic functional group amount depending on the method described in Examples.

The present inventive activated carbon for adsorbing a molecular polar substance is excellent in diffusiveness, adsorption rate, and adsorption amount to a molecular polar substance, and the acidic functional groups imparted to the activated carbon is excellent in the adsorption of a molecular polar substance, therefore the activated carbon is available either in gas or liquid phase.

As one embodiment, the present inventive activated carbon for adsorbing a molecular polar substance is effective for the use in gas phase, and exhibits excellent adsorption property of a molecular polar substance in gas phase such as molecular polar substance-containing gas, malodor component-containing gas, or volatile organic compound (VOC)-containing gas.

As another embodiment, the present inventive activated carbon for adsorbing a molecular polar substance is effective for the use in liquid phase, and exhibits excellent adsorption property of molecular polar substance in gas phase such as molecular polar substance-containing liquid, malodor component-containing liquid, or volatile organic compound-containing liquid.

An example of the use of the activated carbon in gas phase is an adsorption material for ammonia emitted from concrete and drawing materials in exhibition facility such as museums. The activated carbon having phosphoric acid impregnated to it cannot be used at a museum, for a small amount of phosphoric acid emitted from the activated carbon corrodes frames of paintings and the like. The present inventive activated carbon for adsorbing a molecular polar substance is useful because the present inventive activated carbon is comparable to the activated carbon impregnated with phosphoric acid in ammonia adsorption property.

An example of the use of the activated carbon in liquid phase is an adsorption material of chloramine contained in liquid such as tap water. The present inventive activated carbon for adsorbing a molecular polar substance has excellent adsorption rate of a polar substance in liquid phase, allowing a molecular polar substance to be removed effectively in a short time.

The present inventive activated carbon for adsorbing a molecular polar substance can be used in combination with other materials. For example, finely ground activated carbon for adsorbing a molecular polar substance can be attached to natural fibers or synthetic fibers to provide deodorizing function to the fibers. Clothes, insoles, and sweat-removing pads made of the fibers attaching the activated carbon for the adsorption of a molecular polar substance can effectively remove malodorous component, and the deodorizing function can be maintained due to the regenerated adsorption property by washing.

The present inventive activated carbon for adsorbing a molecular polar substance is effective as a filtration material to remove a polar substance from liquid such as tap water, filtration material for filtration or preparation of purified water for artificial dialysis. Also, the present inventive activated carbon for adsorbing a molecular polar substance can be used as water purifiers by filling the activated carbon in a container such as a cartridge.

Hereinafter, the production method for the present inventive activated carbon for adsorbing a molecular polar substance will be described. The production method for the present invention is not particularly restricted to the following production method as long as above described desired physical properties of the activated carbon are achieved, and the production method can be changed as needed. The following manufacturing conditions shows preferable range of the manufacturing conditions, and each manufacturing condition requires to be properly adjusted to obtain activated carbon having desired physical properties.

Materials to be Activated

A material to be activated is a carbide of carbonaceous substance. Any existing carbonaceous substance is used in the present invention. Examples of the carbonaceous substances include nongraphitizing carbon such as wood, sawdust, wood charcoal, coconut shell, cellulosic fiber, synthetic resin (example: phenol resin); easily-graphitizable carbon such as mesophase pitch, pitch coke, petroleum coke, coal coke, needle coke, polyvinyl chloride, polyimide, and polyacrylonitrile; and a mixture thereof. One or more kinds of these carbonaceous substances maybe used. As a preferable carbonaceous substances, a combination of synthetic resin such as phenol resin and other carbonaceous substances (example: paper-phenol resin laminated body), polyacrylonitrile resin, and pitch carbon fibers can be mentioned. In particular, nitrogen-containing carbonaceous substances such as polyacrylonitrile resin is preferable, for such nitrogen-containing carbonaceous substances can increase the amount of acidic functional groups.

Carbonizing Process

A material to be activated is obtained by carbonizing a carbonaceous substance before activation. In the process of carbonization, a carbonaceous substance is heat treated in inert gas such as nitrogen, for example, at 400° C. to 1000° C. for 1 hour to 3 hours.

Alkali Activation Treatment Process

Activation treatment process of the present invention is alkali activation treatment in which an activator agent containing an alkali metal compound and a material to be activated is mixed and then heated in inert gas to prepare activated carbon. In the present invention, the alkali activation treatment employs lower temperature than conventionally employed temperature, allowing to increase both specific surface area and the amount of acidic functional groups.

The alkali activation treatment process of the present invention uses an alkali metal compound as an alkali activation agent. Examples of the alkali metal compounds include alkali metal hydroxides such as potassium hydroxide and sodium hydroxide; an alkali metal carbonates such as potassium carbonate and sodium carbonate; sulphates of alkali metal such as potassium sulfate and sodium sulfate. The alkali metal compound is preferably alkali metal hydroxides, and more preferably potassium hydroxide.

With regard to usage amount of an activation agent, the specific surface area of activated carbon increases as the mixing ratio of an activation agent to a material to be activated increases. On the other hand, as the mixing ratio of an activation agent excessively increases, the density of activated carbon tends to decrease. In the present invention, the mixing ratio of an activation agent is adjusted so as to obtain above described specific surface area. Mass ratio of an activation agent to a material to be activated (mass of activation agent/mass of material to be activated) is preferably 0.5 or more, more preferably 1.0 or more, further preferably 2.0 or more, and preferably 10.0 or less, more preferably 5.0 or less, further preferably 4.0 or less.

Alkali activation treatment of the present invention is performed in an atmosphere of any inert gas exemplified by argon, helium, or nitrogen.

If the alkali activation treatment temperature of the present invention is excessively low, sufficient specific surface area and amount of acidic functional groups cannot be achieved. On the other hand, alkali activation temperature of 800° C. or higher decreases the amount of acidic functional groups. Therefore, the heating temperature of alkali activation treatment is 450° C. or higher, preferably 500° C. or higher, more preferably 550° C. or higher, and preferably lower than 800° C., more preferably 780° C. or lower, further preferably 760° C. or lower. Processing time for the activation treatment is preferably an hour or longer, more preferably 2 hours or longer, and preferably 10 hours or shorter, more preferably 5 hours or shorter. The temperature rising rate is set, in tams of increasing in the specific surface area and the amount of acidic functional groups of the present invention, to preferably 1° C./min or more, more preferably 5° C./min or more, and preferably 20° C./min or less, more preferably 15° C./min or less.

Washing Treatment Process

Washing treatment process is an alkali metal removal process remained in an activated carbon by applying washing treatment with water and washing treatment with inorganic acid to the activated carbon after alkali activation treatment. Repeated washing treatment process over several times enables the activated carbon to have increased removal rate of alkali metal.

Washing Treatment with Water

The temperature of water used for the washing treatment is preferably 20° C. or higher, more preferably 30° C. or higher, and preferably 100° C. or lower, more preferably 95° C. or lower. The washing treatment with water repeats water washing and filtration preferably several times until the pH of a filtrate becomes 7.0 or lower.

Washing with Inorganic Acid

The washing with inorganic acid can use, as an inorganic acid, hydroacids such as hydrochloric acid and hydrofluoric acid; oxyacids such as sulfuric acid, nitric acid, phosphoric acid, and perchloric acid; and preferably hydrochloric acid among them. In tams of raising alkali metal removal rate while maintaining physical properties of the activated carbon, the concentration of the inorganic acid is preferably adjusted so that the inorganic acid is 10 parts by mass to 100 parts by mass based on 100 parts by mass of the activated carbon. The temperature of inorganic acid aqueous solution is preferably set to the temperature range which can enhance alkali metal removal rate in the activated carbon while decreasing volatilization of inorganic acid. The temperature is preferably 20° C. or higher, more preferably 30° C. or higher, and preferably 100° C. or lower, more preferably 95° C. or lower. The washing treatment with inorganic acid repeats inorganic acid washing and filtration several times preferably until remaining amount of potassium in the activated carbon becomes 5000 mg/kg or less (more than 0 mg/kg), more preferably until remaining amount of alkali metal in the activated carbon becomes 2500 mg/kg or less (more than 0 mg/kg), and further preferably until remaining amount of alkali metal in the activated carbon becomes 1000 mg/kg or less (more than 0 mg/kg). Remaining amount of alkali metal can be measured using an ICP atomic emission spectroscopy.

Washing Process with Water

After the wash with the inorganic acid, the activated carbon is washed with water to remove the inorganic acid remaining in the activated carbon. In terms of raising removal rate of the inorganic acid, the temperature of water used for the washing is preferably 20° C. or higher, more preferably 30° C. or higher, further preferably 50° C. or higher, and preferably 100° C. or lower, more preferably 95° C. or lower. The washing treatment with water repeats water washing and filtration several times preferably until the pH of a filtrate becomes 6.5 or higher.

Drying Process

After the washing treatment, the activated carbon may be subjected to a drying process to be dehydrated. The drying process takes any conditions to dehydrate the activated carbon such as heating under atmospherics for 0.5 hours to 24 hours to dry the activated carbon.

The alkali activated carbon obtained by properly adjusting each manufacturing conditions has above described constitution of the present inventive activated carbon for adsorbing a molecular substance.

This application claims the benefit of the priority date of Japanese patent application No. 2019-212411 filed on Nov. 25, 2019. All of the contents of the Japanese patent application No. 2019-212411 filed on Nov. 25, 2019 are incorporated by reference herein.

EXAMPLES

Hereinafter, the present invention is described in more detail with reference to Examples. The present invention is not restricted by the Examples, may be carried out with appropriate modifications to the extent adaptable to the gist of the above and the following description. These variations are included in the technical scope of the present invention.

Example 1

Raw Material to be Activated

A paper-phenol resin laminated body as a carbonaceous substance was carbonized by treating at 700° C. for 2 hours in a nitrogen atmosphere, and thus obtained paper-phenol carbide was used as a raw material to be activated in the next process of alkali activation.

Activation Treatment Process

A commercially available alkali activator (potassium hydroxide solution, concentration: 48.5%) was added to the paper-phenol resin carbide of 1.0 part by weight so that the mass ratio ([mass of alkali component of activator]/[mass of raw material for activation]: herein after, the ratio may be referred to as KOH/C ratio) became 4.0, and the paper-phenol resin carbide was kept for 2 hours at the temperature raised to 600° C. in a nitrogen atmosphere to obtain alkali-activated carbon.

Washing Process with Water

Thus obtained alkali-activated carbon was washed with warm water of 60° C. until the pH of a filtrate became 7.0 or lower.

Washing Process with Inorganic Acid

The activated carbon after washing with water was washed in 5.25 wt % of hydrochloric acid aqueous solution having a temperature adjusted to 60° C. for an hour, and then the mixture was suction filtrated.

Post-Treatment Process (Washing Process with Water)

After the suction filtration, the activated carbon was repeatedly washed and dehydrated using warm water having a temperature of 60° C. until the pH of a filtrate became 6.5 or higher.

Drying Process

The activated carbon obtained after the washing treatment was dried for 24 hours in a drying machine having a temperature set to 115° C., to prepare activated carbon No. 1.

Example 2

Activated carbon No. 2 was prepared by the same method as Example 1 except that a carbonaceous substance was changed to coke from a paper-phenol resin laminated body.

Example 3

Polyacrylonitrile (PAN) as a carbonaceous substance was placed into a muffle furnace (Koyo Thermo Systems Co., Ltd.), the temperature inside the furnace was raised to 650° C. (temperature rising rate: 10° C./min) in a nitrogen atmosphere, then PAN was kept in the furnace under the conditions for 2 hours, and thus obtained PAN resin carbide was used as a raw material to be activated.
Activation Process Alkali activated carbon was obtained from PAN resin carbide by the same method as Example 1 except that the KOH/C ratio was changed to 3.0. Thus obtained alkali activated carbon was subjected to the same washing treatment and drying treatment as Example 1 to prepare activated carbon No. 3.

Example 4

Activated carbon No. 4 was prepared by the same method as Example 1 except that a carbonaceous substance was changed to pitch-based carbon fiber (average fiber diameter: 15 μm, average fiber length: 200 μm) from a paper-phenol resin laminated body.

Example 5

Activated carbon No. 5 was prepared by the same method as Example 1 except that a carbonaceous substance was changed to coke from a paper-phenol resin laminated body and the KOH/C was changed to 2.0.

Example 6

Activated carbon No. 6 was prepared by the same method as Example 1 except that a carbonaceous substance was changed to coke from a paper-phenol resin laminated body.

Example 7

Activated carbon No. 7 was prepared by the same method as Example 1 except that a carbonaceous substance was changed to coke from a paper-phenol resin laminated body and the KOH/C was changed to 5.0.

Example 8

Activated carbon No. 8 was prepared by the same method as Example 1 except that a carbonaceous substance was changed to pitch-based carbon fiber (average fiber diameter: 15 μm, average fiber length: 200 μm) from a paper-phenol resin laminated body and the KOH/C was changed to 3.0.

Example 9

Activated carbon No. 9 was prepared by the same method as Example 1 except that a carbonaceous substance was changed to pitch-based carbon fiber (average fiber diameter: 15 μm, average fiber length: 200 μm) from a paper-phenol resin laminated body and the KOH/C was changed to 5.0.

Comparative Example 1

Alkali activated carbon was obtained by the same method as Example 1 except that the PAN resin carbide obtained in Example 3 was used as a raw material to be activated and the KOH/C ratio was changed to 0.8 and activation temperature was changed to 800° C. in the activation conditions. Thus obtained alkali activated carbon was washed and dried by the same methods as Example 1 to prepare activated carbon No. 10.

Comparative Example 2

Commercially available steam-activated coconut shell carbon (W10-30, MC Evolve Technologies Corporation) was used as activated carbon No. 11.

Comparative Example 3

Commercially available acid impregnated activated carbon (MAXSORB XCA-AS, MC Evolve Technologies Corporation) was used as activated carbon No. 12.

Comparative Example 4

Into a muffle furnace (Koyo Thermo Systems Co., Ltd.), 100 g of activated carbon of Example 6 was placed, the temperature inside the furnace was raised to 600° C. in a nitrogen atmosphere, then the activated carbon was kept in the furnace under the conditions for 2 hours, to prepare activated carbon No. 13.

Comparative Example 5

Coke was used as a raw material to be activated, and commercially available alkali activator was added to the coke so that the KOH/C became 1.6. Thus obtained mixture was then raised to 800° C. in an atmosphere of nitrogen and kept at the temperature for 2 hours, and alkali activated carbon was obtained. Thus obtained alkali activated carbon was washed and dried by the same method as Example 1 to prepare activated carbon No. 14.

Comparative Example 6

Activated carbon No. 15 was prepared by the same method as Comparative Example 5 except that a carbonaceous substance was changed to pitch-based carbon fiber (average fiber diameter: 15 μm, average fiber length: 200 μm) from coke and the KOH/C was changed to 1.7.

Comparative Example 7

After 100 g of activated carbon of Comparative Example 2 was placed into a rotary kiln (Tanaka Tec CO., Ltd.), internal temperature of the furnace was raised to 500° C. while air flowing into the furnace at a flow rate of 5 L/min, and oxidizing treatment was made to the activated carbon by keeping at the temperature for 3 hours to prepare activated carbon No. 16.

Comparative Example 8

After 100 g of activated carbon of Comparative Example 2 was placed into a rotary kiln (Tanaka Tec CO., Ltd.), and internal temperature of the furnace was raised to 500° C. while air flowing into the furnace at a flow rate of 0.5 L/min.

After that, the activated carbon was oxidized by being kept at the temperature for 3 hours while flowing air at a rate of 0.5 L/min and pure water at a rate 3.62 g/min so that the relative humidity inside furnace became 90% to prepare activated carbon No. 17.

Comparative Example 9

After 100 g of activated carbon of Comparative Example 2 was placed into a beaker, the activated carbon was subjected to 3 hours oxidation treatment in 20% nitric acid aqueous solution of 60° C. with agitation at 300 rpm. After the oxidation treatment, the oxidized activated carbon was washed with warm water of 60° C. to remove nitric acid aqueous solution while being suction filtrated, and the activated carbon after the filtration was boiled in hot water for an hour. After the boiling, the activated carbon was repeatedly washed and dehydrated with warm water of 60° C. until the pH of a filtrate became 6.5 or higher. Thus obtained activated carbon was dried in a dryer having the temperature set to 115° C. for 24 hours to prepare activated carbon No. 18.

Comparative Example 10

Steam-activated coconut shell carbon having high specific surface area (primary crushing product of Z10-30HS, MC Evolve Technologies Corporation) was used as activated carbon No. 19.

Each sample of the activated carbons above described was evaluated dependent on the following conditions.

Specific Surface Area

The sample (0.2 g) was vacuum dried at 250° C. and then the adsorption amount of nitrogen gas was measured in an atmosphere of liquid nitrogen (−196° C.) using a nitrogen absorption device (ASAP-2420, Micromeritics Corp.) to obtain a nitrogen adsorption isotherm, and specific surface area ($m^2/g$) was obtained by the BET method.

Total Volume of Pore

Total volume of pore (mL/g) was calculated from the adsorption amount of nitrogen when relative pressure (P/P0) was 0.93 in a nitrogen adsorption isotherm.

Average Pore Diameter

Based on the assumption that the pore shape of the activated carbon was cylindrical, an average pore diameter was calculated according to the following formula:

Average diameter of fine pore (nm)=4×total volume of fine pore (mL/g)/specific surface area ($m^2/g$)×1000

Total Amount of Acidic Functional Group

The amount of acidic functional group was determined following the Boehm method (Literature "H. P. Boehm, Adzan. Catal, 16,179(1966)"). Specifically, 1 g of the activated carbon (Examples 1 to 9) or 2 g of the activated carbon (Comparative Examples 1, 2, 4 to 10) was mixed with 50 mL of sodium ethoxide solution (0.1 moL/L) to prepare a mixture and then the activated carbon was stirred at 500 rpm for 2 hours. After 24 hours aging, the activated carbon was further stirred for 30 minutes and then separated by filtration. Then, 0.1 mol/L of hydrochloric acid was added dropwise to a filtrate of 25 mL, and titration amount of hydrochloric acid at the pH turned to 4.0 was measured. As a blank test, 0.1 mol/L of hydrochloric acid was added dropwise to 25 mL of sodium ethoxide solution (0.1 moL/L), and titration amount of hydrochloric acid at the pH turned to 4.0 was measured. The amount of acidic functional group (meq/g) was calculated according to the following formula (1).

[Formula 1]

$$\text{Amout of acidic functional group (meq/g)} = \frac{(a-b) \times 0.1}{S \times 25/50} \quad (1)$$

a: amount of hydrochloric acid at blank test
b: amount of hydrochloric acid when sample of activated carbon is reacted with sodium ethoxide solution
S: mass of sample (g)

Detection of Each Acidic Functional Group

Instead of 0.1 mol/1000 mL of NaOEt, 0.1 mol/1000 mL of NaOH, 0.05 mol/1000 mL of $Na_2CO_3$, or 0.1 mol/1000 mL of $NaHCO_3$ was used to determine each acidic functional group, and the evaluation of each acidic functional group was carried out by the same method as the evaluation of total acidic functional group amount. Each acidic functional group was calculated according to the following formulas.

TABLE 1

| Reagent Name | Blank (mL) | Sample (mL) | Amount of surface functional group (meq/g) | |
|---|---|---|---|---|
| NaOEt | a1 | b1 | a1 − b1 = d | Acidic surface functional group amount = d × 0.1 |
| NaOH | a2 | b2 | a2 − b2 = e | R—O = (d − e) × 0.1 |
| $Na_2CO_3$ | a3 | b3 | a3 − b3 = f | R—OH = (e − f) × 0.1 |
| $NaHCO_3$ | a4 | b4 | a4 − b4 = g | R—OCO = (f − g) × 0.1 |
| | | | | R—COOH = g × 0.1 |

Based on the quantification method of functional group amount of activated carbon described in the literatures "Otowa, 1996, Hyoumen, 34[2], 62" or "Catal, 16,179 (1966)", 1 g (Examples 1 to 9) or 2 g (Comparative Examples 1, 2, 4 to 10) of activated carbon was placed in an erlenmeyer flask (capacity: 100 mL), respectively 50 mL of N/10 alkali reagent ((a) sodium hydrogen carbonate, (b) sodium carbonate, (c) sodium hydroxide, (d) sodium ethoxide) was added to the flask to prepare a mixture, and the mixture was shook for 24 hours. Then, unreacted alkali reagent was titrated with N/10 hydrochloric acid, and the amount of each functional group was determined by subtracting titration amount required to neutralize the rest of the alkali reagent from the total amount of the alkali reagent, for a carboxy group reacts with the reagent all of (a) to (d), a lactone group reacts with (b) to (d), a hydroxy group reacts with (c) to (d), and quinone group reacts with (d).

Amount of Basic Functional Group

The amount of basic functional groups was determined by back titration, the same titration method used to measure the amount of acidic functional groups. Specifically, 1 g (Examples 1 to 9) or 2 g (Comparative Examples 1, 2, 4 to 10) of the activated carbon was mixed with 50 mL of hydrochloric acid (0.1 mol/L) to prepare a mixture, and then the activated carbon was stirred at 500 rpm for 2 hours. After 24 hours aging, the activated carbon was further stirred for 30 minutes and then separated by filtration. Then, 0.1 mol/L of sodium hydroxide was added dropwise to a filtrate of 25 mL, and titer volume of sodium hydroxide at the pH turned to 8.0 was measured. As a blank test, 0.1 mol/L of sodium hydroxide was added dropwise to above-described 25 mL of hydrochloric acid (0.1 mol/L), and titer volume of sodium hydroxide at the pH turned to 8.0 was measured. The amount of basic functional group (meq/g) was calculated from the following formula (2).

[Formula 2]

$$\text{Amount of basic functional group (meq/g)} = \frac{(a-b) \times 0.1}{S \times 25/50} \quad (2)$$

a: amount of sodium hydroxide at blank test
b: amount of sodium hydroxide when sample of activated carbon is reacted with sodium ethoxide solution
S: mass of sample (g)

Ratio of Acidic Functional Group

The ratio of acidic functional group was calculated from above described amount of acidic functional group (meq/g) and basic functional group (meq/g).

Amount of acidic functional group/(amount of acidic functional group+amount of basic functional group)×100

Amount of Acidic Functional Group Per Specific Surface Area

The amount of acidic functional group per specific surface area (μeq/m²) was obtained from above described specific surface area (m²/g) and the amount of acidic functional group (meq/g).

Amount of acidic functional group (meq/g)/specific surface area (m²/g)×1000(unit conversion)

Amount of Acidic Functional Group and Active Surface Area after Oxidation

For the calculation of acidic functional group and active surface area after oxidation, unground activated carbon fiber of Examples 4 and 8 to 9, and Comparative Example 6; and granular shaped carbon of Examples 2, 3, and 5 to 7; and Comparative Examples 1, 2, 4, 5, and 7 to 10 ground with a mortar to have the activated carbon sized 250 μm or less were oxidized at 300° C. for 24 hours in an air atmosphere. The amount of acidic surface functional groups after oxidation (meq/g) was calculated dependent on the following formula, and active surface area (m²/g) was calculated with the occupying area of a molecular of oxygen-containing compound regarded to be 0.083 nm².

Active surface area (m²/g)=$a \times 10^{-3} \times b \times c \times 10^{-18}$ [Formula 3]

a: Amount of acidic surface functional group after oxidation (meq/g)
b: $6.02 \times 10^{23}$ (mol$^{-1}$) Avogadro number
c: 0.083 (nm²) of area occupied by a molecular of oxygen-containing compound Evaluation of Ammonia Adsorption Ground state of activated carbon to the size of 250 μm or less was placed in a 5-liter Tedlar bag. The amount of activated carbon placed in the bag is as follows.

Examples 1, 2, 4, and Comparative Example 3: 0.01 g, 0.02 g, 0.03 g
Example 3: 0.005 g, 0.01 g, 0.02 g
Comparative Example 1: 0.03 g, 0.06 g, 0.09 g
Comparative Example 2: 0.1 g, 0.3 g, 0.5 g After the activated carbon was placed into the Tedlar bags, air was removed from the Tedlar bags using a vacuum pump, and the Tedlar bags were filled with dried air of 3 L. Then, ammonia water (KISHIDA CHEMICAL Co., Ltd., purity: 28%) was injected to the Tedlar bags so that the initial concentration of ammonia water became 100 ppm, and the Tedlar bags were allowed to stand for 24 hours in a thermostatic chamber set to 25° C. After that, the concentration of ammonia in the Tedlar bags was quantified using a detecting tube (GASTEC CORPORATION), and an adsorption isotherm was obtained. The adsorption amount of ammonia at equilibrium concentration of 10 ppm was obtained from the Freundlich equation fit to the adsorption isotherm.

TABLE 2A

| No. | | Raw material | Activation method · post processing | KOH/C ratio | Activation temperature ° C. | Specific surface area m²/g | Total pore volume cm³/g | Average pore diameter nm |
|---|---|---|---|---|---|---|---|---|
| 1 | Example 1 | Paper-phenol resin carbide | Alkali activation | 4 | 600 | 1893 | 0.87 | 1.84 |
| 2 | Example 2 | Petroleum coke | Alkali activation | 4 | 600 | 1776 | 0.86 | 1.94 |
| 3 | Example 3 | PAN resin | Alkali activation | 3 | 600 | 1821 | 0.90 | 1.97 |
| 4 | Example 4 | Coal pitch based carbon fiber | Alkali activation | 4 | 600 | 2170 | 1.09 | 2.01 |
| 10 | Comparative Example 1 | PAN resin | Alkali activation | 0.8 | 800 | 2149 | 0.93 | 1.73 |
| 11 | Comparative Example 2 | Coconut shell activated carbon (W10-30) | Steam activation | — | — | 1217 | 0.51 | 1.69 |
| 12 | Comparative Example 3 | MAXSORB XCA-AS | Steam activated coconut shell carbon-phosphoric acid impregnation | — | — | — | — | — |

TABLE 2B

| No. | Amount of acidic functional groups | | | | | Amount of acidic functional group per specific surface area μeq/m² | Amount of basic functional group meq/g | Acidic functional group/ (acidic functional group + basic functional group) % | Amount of acidic functional group after oxidation meq/g | Active surface area m²/g | Ammonia adsorption amount (at 10 ppm) mg/g |
|---|---|---|---|---|---|---|---|---|---|---|---|
| | Total meq/g | R=O group amount meq/g | R—OH group amount meq/g | R—OCO group amount meq/g | R—COOH group amount meq/g | | | | | | |
| 1 | 2.44 | 0.00 | 0.96 | 0.54 | 0.95 | 1.29 | 0.09 | 96 | — | — | 13.8 |
| 2 | 3.07 | 0.00 | 1.22 | 0.58 | 1.27 | 1.73 | 0.05 | 98 | 3.85 | 192 | 17.6 |
| 3 | 3.00 | 0.00 | 1.25 | 0.67 | 1.08 | 1.65 | 0.17 | 95 | 3.83 | 191 | 22.7 |
| 4 | 3.01 | 0.00 | 1.20 | 0.65 | 1.16 | 1.39 | 0.05 | 98 | 3.98 | 199 | 15.8 |
| 10 | 0.74 | 0.00 | 0.46 | 0.17 | 0.10 | 0.34 | 0.68 | 52 | 1.27 | 64 | 5.5 |
| 11 | 0.11 | 0.00 | 0.10 | 0.01 | 0.00 | 0.09 | 0.40 | 22 | 0.41 | 21 | 0.3 |
| 12 | — | — | — | — | — | — | — | — | — | — | 18.2 |

Activated carbon Nos. 1 to 4 had high specific surface area of 1500 m²/g or more as well as large amount of acidic functional groups of 2.1 meq/g or more and small amount of basic functional groups of 0.2 meq/g or less, therefore, activated carbon Nos. 1 to 4 can be said to be the activated carbon for adsorbing a molecular polar substance satisfying the requirements of the present invention. These activated carbons had acidic functional groups in an amount of 3.15 meq/g or more, and active surface area of 180 m²/g or more after oxidation. These activated carbons Nos. 1 to 4 had ammonia adsorption amount of 10.0 mg/g or more and the activated carbons showed superior adsorption property of ammonia to the activated carbons of Comparative Examples Nos. 10 and 11.

Activated carbon No. 10 was the alkali-activated carbon obtained by the conventional activation treatment conducted at high temperature. This activated carbon had specific surface area of 2000 m²/g or more, however, the activated carbon had small adsorption amount of ammonia due to decreased amount of acidic functional groups.

Activated carbon No. 11 was coconut shell activated carbon obtained by steam activation treatment, and the activated carbon scarcely adsorbed ammonia because of its decreased acidic functional group amount. Activated carbon No. 12 was the activated carbon having chemical agent impregnated to it, the activated carbon had large ammonia adsorption amount as an effect of the chemical agent, however, the activated carbon was not reusable.

As shown in FIG. 1, the activated carbon Nos. 1 to 4 (Examples 1 to 4) satisfying the requirements of the present invention showed excellent ammonia adsorption property because the activated carbons had higher ammonia adsorption amount by two times or more compared to the activated carbon No. 10 (Comparative Example 1) prepared by a conventional method. The activated carbon Nos. 2 to 4 had equal excellent ammonia adsorption property to activated carbon No. 12 (Comparative Example 3) having the chemical agent impregnated to it.

There was a correlation between the amount of acidic functional groups and the amount of basic functional groups as shown in FIGS. 2 to 4 and 7, that is, the amount of basic functional groups decreases with the increase in the amount of acidic functional groups. Further, FIG. 6 shows the tendency that the amount of ammonia adsorption increases with the increase in the amount of acidic functional groups per specific surface area of activated carbon, indicating that enlarged specific surface area of activated carbon as well as the increase in the amount of acidic functional groups are effective for the improvement of ammonia adsorption property.

Evaluation of Chloramine Adsorption

The activated carbon having adjusted grain size was placed in a graduated flask (capacity: 100 mL, amber) with a stopper. Activated carbons of Examples 4, 8 to 9, and Comparative Example 6 was unground activated carbon fiber; and activated carbons of Example 2, 3, 5 to 7; and Comparative Example 1, 2, 4, 5, and 7 to 10 were particulate activated carbon classified by using a sieve with the opening of 53 to 125 μm. The amount of the activated carbons placed in a flask was as follows.

Examples 2 to 9: 0.01 g, 0.03 g, 0.05 g, 0.1 g, 0.2 g

Comparative Examples 2, 8 to 10: 0.1 g, 0.3 g, 0.5 g, 1.0 g, 1.5 g

Comparative Examples 1, 4 to 7: 0.05 g, 0.1 g, 0.2 g, 0.3 g, 0.5 g

After placing the activated carbons, 100 mL of a chloramine solution (monochloramine) adjusted to the concentration of approximately 100 ppm was added to the activated carbon, and the activated carbon was stirred for 2 hours at 200 rpm in a thermostatic chamber set to 25° C. Then the activated carbon was filtrated by using a syringe filter to obtain a filtrate.

In a test tube (capacity: 10 mL) with a stopper, 0.5 mL of phosphate buffer was placed, and the total volume of the solution was increased to 10 mL by adding above mentioned filtrate diluted to a predetermined concentration to the phosphate buffer. Then, 0.1 g of DPD reagent, N,N-diethyl-p-phenylenediamine (KANTO CHEMICAL CO., INC.), was added to the solution and mixed, and colored solution was obtained. The concentration of free residual chlorine of the colored solution was measured using a residual chlorine meter (HACH Corp.).

After the measurement, 0.1 g of potassium iodide (KISHIDA CHEMICAL Co., Ltd.) was added to the tested solution and dissolved, then the solution was stood still for 2 minutes, and residual chlorine concentration was measured using a residual chlorine meter. Combined residual chlorine (chloramine) concentration (mg/L) was calculated from the difference of above described residual chlorine concentration and free residual chlorine concentration, and an adsorption isotherm was obtained from the relationship between residual chloramine concentration (mg/L) and removals of chloramine (mg/g). Removals of chloramine at the residual concentration of 3 ppm was obtained from the Freundlich equation fit to the adsorption isotherm.

Evaluation of Chloramine Removal Rate

The activated carbon weighed amount of 0.1 g and having adjusted grain size was placed in a graduated flask (capacity: 100 mL, amber) with a stopper. Activated carbon having adjusted grain size was unground activated carbon fiber in the case of Example 4 and Comparative Example 6; and was granular activated carbon classified by a sieve with the opening of 53 to 125 μm in the case of Examples 2, 3, and 5 to 7, and Comparative Examples 1, 2, 4, 5, and 7 to 10.

After placing the activated carbon to a flask, 100 mL of chloramine (monochloramine) aqueous solution adjusted to the concentration of approximately 100 ppm was poured into the flask. The activated carbon was stirred at 200 rpm in a thermostatic chamber set to 25° C. for the following predetermined minutes, 5 mins, 10 mins, 20 mins, 30 mins, 60 mins, 90 mins, or 120 mins, and the concentration (mg/L) of combined residual chlorine (chloramine) was calculated by the same method as described above. Thus obtained residual chloramine concentration is "(C)", initial chloramine concentration is "($C_0$)", and stirring time (reaction time) is "t" in the following equation, chloramine removal ratio per unit time was calculated from the equation, and the rate was defined as chloramine removal rete (v, %/min).

$$V\ (\%/\text{min}) = \{(C_0 - C)/C_0 \times 100\}/t$$

TABLE 3A

| No. | | Raw material | Activation method · post processing | KOH/C ratio | Activation temperature ° C. | Specific surface area m²/g | Total pore volume cm³/g | Average pore diameter nm |
|---|---|---|---|---|---|---|---|---|
| 2 | Example 2 | Petroleum coke | Alkali activation | 4.0 | 600 | 1776 | 0.86 | 1.94 |
| 3 | Example 3 | PAN resin | Alkali activation | 3.0 | 600 | 1821 | 0.90 | 1.97 |
| 4 | Example 4 | Coal pitch based carbon fiber | Alkali activation | 4.0 | 600 | 2170 | 1.09 | 2.01 |
| 5 | Example 5 | Petroleum coke | Alkali activation | 2.0 | 600 | 1684 | 0.79 | 1.88 |
| 6 | Example 6 | Petroleum coke | Alkali activation | 4.0 | 600 | 1852 | 0.89 | 1.92 |
| 7 | Example 7 | Petroleum coke | Alkali activation | 5.0 | 600 | 2395 | 1.16 | 1.94 |
| 8 | Example 8 | Coal pitch based carbon fiber | Alkali activation | 3.0 | 600 | 1931 | 0.92 | 1.91 |
| 9 | Example 9 | Coal pitch based carbon fiber | Alkali activation | 5.0 | 600 | 2720 | 1.42 | 2.09 |
| 10 | Comparative Example 1 | PAN resin | Alkali activation | 0.8 | 800 | 2149 | 0.93 | 1.73 |
| 11 | Comparative Example 2 | Coconut shell activated carbon (W10-30) | Steam activation | — | — | 1217 | 0.51 | 1.68 |
| 13 | Comparative Example 4 | Petroleum coke | Alkali activation-heat treatment | 4.0 | 600 | 1865 | 0.87 | 1.87 |
| 14 | Comparative Example 5 | Petroleum coke | Alkali activation | 1.6 | 800 | 1881 | 0.82 | 1.74 |
| 15 | Comparative Example 6 | Coal pitch based carbon fiber | Alkali activation | 1.7 | 800 | 1850 | 0.75 | 1.62 |
| 16 | Comparative Example 7 | Coconut shell activated carbon (W10-30) | Steam activation-oxidation treatment | — | — | 1469 | 0.66 | 1.80 |
| 17 | Comparative Example 8 | Coconut shell activated carbon (W10-30) | Steam activation-oxidation treatment | — | — | 1273 | 0.54 | 1.71 |
| 18 | Comparative Example 9 | Coconut shell activated carbon (W10-30) | Steam activation-nitric acid treatment | — | — | 1145 | 0.48 | 1.68 |
| 19 | Comparative Example 10 | Coconut shell activated carbon (Z10-30HS) | Steam activation | — | — | 1842 | 0.86 | 1.87 |

TABLE 3B

| | Amount of acidic functional groups | | | | | Amount of acidic functional group per specific surface area μeq/m² | Amount of basic functional group meq/g | Acidic functional group/ (acidic functional group + basic functional group) % | Amount of acidic functional group after oxidation meq/g | Active surface area m²/g | Chloramine removal rate (for 5 mins from the start of reaction) %/min | Chloramine removal amount (at 3 ppm) mg/g |
|---|---|---|---|---|---|---|---|---|---|---|---|---|
| No. | Total meq/g | R=O group amount meq/g | R—OH group amount meq/g | R—OCO group amount meq/g | R—COOH group amount meq/g | | | | | | | |
| 2 | 3.07 | 0.00 | 1.22 | 0.58 | 1.27 | 1.73 | 0.05 | 98 | 3.85 | 192 | 8.2 | 86.9 |
| 3 | 3.00 | 0.00 | 1.25 | 0.67 | 1.08 | 1.65 | 0.17 | 95 | 3.83 | 191 | 8.0 | 105.2 |
| 4 | 3.01 | 0.00 | 1.20 | 0.65 | 1.16 | 1.39 | 0.05 | 98 | 3.98 | 199 | 10.8 | 152.9 |

TABLE 3B-continued

| | Amount of acidic functional groups | | | | Amount of acidic functional group per specific surface area µeq/m² | Amount of basic functional group meq/g | Acidic functional group/ (acidic functional group + basic functional group) % | Amount of acidic functional group after oxidation meq/g | Active surface area m²/g | Chloramine removal rate (for 5 mins from the start of reaction) %/min | Chloramine removal amount (at 3 ppm) mg/g |
|---|---|---|---|---|---|---|---|---|---|---|---|
| No. | Total meq/g | R=O group amount meq/g | R—OH group amount meq/g | R—OCO group amount meq/g | R—COOH group amount meq/g | | | | | | | |
| 5 | 2.10 | 0.00 | 0.93 | 0.46 | 0.71 | 1.24 | 0.13 | 94 | 3.88 | 194 | 6.8 | 73.0 |
| 6 | 3.12 | 0.00 | 1.25 | 0.52 | 1.35 | 1.69 | 0.05 | 98 | 3.85 | 192 | 8.5 | 81.5 |
| 7 | 2.73 | 0.00 | 1.13 | 0.65 | 0.95 | 1.14 | 0.10 | 97 | 4.07 | 203 | 6.2 | 89.8 |
| 8 | 2.67 | 0.00 | 1.07 | 0.65 | 0.95 | 1.38 | 0.04 | 99 | 3.65 | 182 | — | 103.8 |
| 9 | 2.65 | 0.00 | 1.11 | 0.63 | 0.90 | 0.97 | 0.12 | 96 | 3.91 | 196 | — | 161.5 |
| 10 | 0.74 | 0.00 | 0.46 | 0.17 | 0.10 | 0.34 | 0.68 | 52 | 1.27 | 64 | 3.4 | 58.3 |
| 11 | 0.11 | 0.00 | 0.10 | 0.01 | 0.00 | 0.09 | 0.40 | 22 | 0.41 | 21 | 1.9 | 7.6 |
| 13 | 1.05 | 0.00 | 0.54 | 0.25 | 0.26 | 0.56 | 0.23 | 82 | 3.15 | 158 | 3.5 | 26.2 |
| 14 | 0.63 | 0.00 | 0.41 | 0.16 | 0.06 | 0.34 | 0.44 | 59 | 1.66 | 83 | 1.9 | 18.2 |
| 15 | 0.82 | 0.00 | 0.41 | 0.24 | 0.17 | 0.44 | 0.36 | 70 | 1.59 | 80 | 3.4 | 34.0 |
| 16 | 1.90 | 0.00 | 0.75 | 0.42 | 0.73 | 1.30 | 0.11 | 95 | 2.17 | 109 | 2.8 | 19.1 |
| 17 | 0.67 | 0.00 | 0.35 | 0.18 | 0.15 | 0.53 | 0.22 | 75 | 0.89 | 44 | 2.3 | 6.2 |
| 18 | 0.88 | 0.00 | 0.39 | 0.21 | 0.28 | 0.77 | 0.18 | 83 | 1.20 | 60 | 2.8 | 8.5 |
| 19 | 0.30 | 0.01 | 0.19 | 0.06 | 0.04 | 0.16 | 0.38 | 44 | 0.53 | 26 | 1.9 | 6.9 |

Activated carbon Nos. 2 to 9 had high specific surface area specifically with its specific surface area of 1500 m²/g or more, large acidic functional group amount of 2.1 meq/g or more, and small basic functional group amount of 0.2 meq/g or less, therefore, the activated carbon Nos. 2 to 9 can be said to be the activated carbon for adsorbing a molecular polar substance satisfying the requirements of the present invention. In addition, these activated carbons have acidic functional group amount of 3.15 meq/g or more, and specific surface area of 180 m²/g or more after oxidation.

The activated carbon Nos. 2 to 9 also had chloramine removal amount of 30 mg/g or more, and chloramine removal rate of 6%/min or more, and the activated carbons showed superior adsorption ability to the activated carbons of Comparative Example Nos. 10, 11, and 13 to 19.

The activated carbon Nos. 10, 11, and 13 to 19 had specific surface area of 1000 m²/g or more, however, these are the examples of activated carbon having less amount of acidic functional groups and small active surface area. These activated carbons could remove chloramine in an insufficient amount, and the activated carbons had low chloramine removal rate.

FIGS. 8 to 11 show the relationships between each physical property of the activated carbons and chloramine removal amount. FIGS. 12 to 15 show the relationships between each physical property of the activated carbons and chloramine removal rate.

As shown in FIGS. 8 and 12, there were no correlation between the specific surface area and chloramine removal amount and chloramine removal rate.

As shown in FIG. 9, there is a tendency that chloramine removal amount increases with raised amount of acidic functional groups. Also, FIG. 13 shows the correlation between the amount of acidic functional groups and chloramine removal rate.

FIGS. 9, 10, 13, and 14 show the correlation between the amount of acidic functional groups and basic functional groups, and the amount of basic functional groups tends to decrease as the amount of acidic functional groups increases.

As shown in FIGS. 9, 11, 13, and 15, the activated carbons Nos. 2 to 9 show excellent adsorption property to chloramine.

FIG. 16 is the graph showing the relationship between chloramine removal rate and chloramine removal amount.

As shown in FIG. 16, the activated carbons Nos. 2 to 7 are excellent in their catalytic performance.

The invention claimed is:

1. An activated carbon for adsorbing a molecular polar substance obtained by an alkali activation method, wherein the activated carbon has an acidic functional group in an amount of 2.1 meq/g or more, a basic functional group in an amount of more than 0 to 0.3 meq/g, and a specific surface area of 1000 to 4000 m²/g.

2. The activated carbon for adsorbing a molecular polar substance according to claim 1, wherein the acidic functional group contains a hydroxy group and a carboxy group in a total amount of 0.6 meq/g or more.

3. The activated carbon for adsorbing a molecular polar substance according to claim 1, wherein a ratio of the acidic functional group amount to the total of the acidic functional group amount and the basic functional group amount is 70% or more.

4. The activated carbon for adsorbing a molecular polar substance according to claim 1, wherein the activated carbon has the acidic functional group of 0.7 µeq/m² or more per specific surface area.

5. The activated carbon for adsorbing a molecular polar substance according to claim 1, wherein the activated carbon has no chemical agent impregnated pores.

6. The activated carbon for adsorbing a molecular polar substance according to claim 1, wherein the activated carbon has an active surface area of 180 m²/g or more.

7. The activated carbon for adsorbing a molecular polar substance according to claim 1, wherein the activated carbon is other than a polyacrylonitrile-based activated carbon fiber.

* * * * *